United States Patent [19]

Kneuper et al.

[11] Patent Number: 5,387,719
[45] Date of Patent: Feb. 7, 1995

[54] PREPARATION OF ALDEHYDES

[75] Inventors: Heinz-Josef Kneuper, Mannheim; Michael Roeper, Wachenheim; Rocco Paciello, Bad Duerkheim, all of Germany

[73] Assignee: BASF Aktiengesellschaft, Ludwigshafen, Germany

[21] Appl. No.: 120,427

[22] Filed: Sep. 14, 1993

[30] Foreign Application Priority Data

Sep. 16, 1992 [DE] Germany .............. 4230871
May 14, 1993 [DE] Germany .............. 4316180

[51] Int. Cl.$^6$ ............ C07C 45/00; C07C 45/50; C07C 45/78
[52] U.S. Cl. .................. 568/455; 568/451; 568/492; 252/512
[58] Field of Search ........... 568/451, 454, 492, 455; 252/514, 512

[56] References Cited

U.S. PATENT DOCUMENTS

| | | | |
|---|---|---|---|
| 3,579,575 | 5/1971 | Bouniot | 560/530 |
| 3,755,393 | 8/1973 | Kniese et al. | 568/492 |
| 3,920,754 | 11/1975 | Wu et al. | 568/454 |
| 3,932,523 | 1/1976 | Strohmeyer et al. | 568/454 |
| 3,984,478 | 10/1976 | Homeier | 568/454 |
| 4,113,754 | 9/1978 | Kummer et al. | 568/492 |
| 4,221,743 | 9/1980 | Halstead | 568/45 |
| 4,225,458 | 9/1980 | Huang | 252/413 |
| 4,292,196 | 9/1981 | Homeier et al. | 252/412 |
| 4,298,499 | 11/1981 | Imai | 252/414 |
| 4,400,547 | 8/1983 | Dawes et al. | 568/454 |
| 4,528,403 | 7/1985 | Tano et al. | 568/454 |

FOREIGN PATENT DOCUMENTS

| | | |
|---|---|---|
| 2604545 | 8/1977 | Germany . |
| 3338340 | 5/1984 | Germany . |
| 1296435 | 11/1972 | United Kingdom . |
| 1566716 | 4/1980 | United Kingdom . |
| WO8203856 | 11/1982 | WIPO .............. 568/454 |

OTHER PUBLICATIONS

J. Falbe, Ed., New Syntheses With Carbon Monoxide, Springer, Berlin 1980 pp. 55 ff.-38, 95 FF.
Chem. Ber. 102 (1969, 2238 Tetrahedron Lett. 29 (1968) 3261.
Hydrocarbon Process. (1975) 85-86 Chem. Ber. 123 (1990) 1953.

*Primary Examiner*—Werren B. Lone
*Attorney, Agent, or Firm*—Keil & Weinkauf

[57] ABSTRACT

A process for the preparation of aldehydes by hydroformylation of olefins having more than 7 carbon atoms, comprising hydroformylation by means of a rhodium catalyst dissolved homogeneously in the reaction medium, removal of the rhodium catalyst from the hydroformylation reaction product, and recycling of the rhodium separated off from the hydroformylation product into the hydroformylation step, in which the rhodium catalyst is extracted from the hydroformylation product into the aqueous phase by means of an aqueous solution of a nitrogen-containing complexing agent from the group comprising of sulfonated pyridines, sulfonated quinolines, substituted or unsubstituted, sulfonated or sulfonated substituent-carrying 2,2'-bipyridines, 1,10-phenanthrolines, 2,2'-biquinolines, 2,2',6',2"-terpyridines and porphines, and/or from the group comprising of carboxylated pyridines, carboxylated quinolines, substituted or unsubstituted, carboxylated or carboxylated substituent-carrying 2,2'-bipyridines, 1,10-phenanthrolines, 2,2'-biquinolines, 2,2',6',2"-terpyridines and porphines, and the aqueous, rhodium-containing extract is recycled into the hydroformylation step.

5 Claims, No Drawings

PREPARATION OF ALDEHYDES

The present invention relates to a process for the preparation of aldehydes by hydroformylation of olefins having more than 7 carbon atoms, comprising hydroformylation by means of a rhodium catalyst dissolved homogeneously in the reaction medium, removal of the rhodium catalyst from the hydroformylation reaction product, and recycling of the rhodium separated off from the hydroformylation product into the hydroformylation step.

The hydroformylation of olefins by means of carbon monoxide and hydrogen in the presence of transition-metal catalysts is known. While α-olefins can be hydroformylated very well using rhodium-containing, phosphine-modified catalysts (cf. J. Falbe, Ed., New Syntheses With Carbon Monoxide, Springer, Berlin, 1980, pp. 55 ff), this catalyst system is not very suitable for internal olefins and internal, branched olefins and for olefins having more than 7 carbon atoms (cf. Falbe, pp. 95 ff). Thus, internal carbon-carbon double bonds are hydroformylated only very slowly in the presence of a catalyst of this type. Since the separation of the hydroformylation product from the catalyst homogeneously dissolved in the reaction system is generally carried out by distillation and since the boiling point of the aldehyde formed in the hydroformylation increases with increasing number of carbons and chain length to temperatures at which the rhodium-containing catalyst decomposes, this hydroformylation method is not economical for the hydroformylation of olefins having more than 7 carbon atoms. In the hydroformylation of polymeric olefins, for example polyisobutene, the noble metal-containing catalyst cannot be recovered in reusable form.

By contrast, internal and internal, branched olefins can advantageously be hydroformylated using so-called "naked" rhodium, i.e. rhodium compounds which are dissolved homogeneously in the hydroformylation medium which have not been modified by means of phosphorus-containing ligands, such as phosphines or phosphites. These rhodium catalysts which have not been modified by means of phosphines or phosphites, and their suitability as catalysts for the hydroformylation of the abovementioned classes of olefin, are known (see Falbe, pp. 38 ff.). The term "naked rhodium" or "naked rhodium catalysts" is used in this application for rhodium hydroformylation catalysts which, in contrast to conventional rhodium hydroformylation catalysts, have not been modified by means of ligands under the conditions of the hydroformylation, in particular have not been modified by means of phosphorus-containing ligands, such as phosphine or phosphite ligands. For the purposes of the present invention, ligands do not include carbonyl or hydrido ligands. It is assumed in the specialist literature (see Falbe, pp. 38 ff.) that the rhodium compound $HRh(CO)_4$ is the catalytically active rhodium species in hydroformylation using naked rhodium catalysts, although this has not been unambiguously demonstrated due to the large number of chemical reactions which occur alongside one another in the hydroformylation reaction zone. Merely for reasons of simplicity, we will also use this assumption in this application, without thereby restricting the scope of the present application should in the future another rhodium species than the above prove to be the actual catalytically active one. Under the conditions of the hydroformylation reaction, the naked rhodium catalysts form from rhodium compounds, for example rhodium salts, such as rhodium(III) chloride, rhodium(III) nitrate, rhodium(III) acetate, rhodium(II) acetate, rhodium(III) sulfate or rhodium(III) ammoniumchloride, from rhodium chalcogenides, such as rhodium(III) oxide or rhodium(III) sulfide, from salts of rhodium oxoacids, for example from rhodates, from rhodium carbonyl compounds, such as $Rh_4(CO)_{12}$ or $Rh_6(CO)_{16}$, or from organorhodium compounds, such as dicarbonylrhodium acetylacetonate, cyclooctadienylrhodium acetate or chloride, in the presence of $CO/H_2$ mixtures, which are generally known as synthesis gas. For carrying out hydroformylations using "naked" rhodium, reference is made at this point for illustrative purposes to the following publications: U.S. Pat. No. 4,400,547, DE-A 33 38 340, DE-A 26 04 545, WO 82/03856, Chem. Ber. 102 (1969) 2238, Tetrahedron Lett. 29 (1968) 3261, and Hydrocarbon Process. (1975) 85–86.

However, hydroformylation using naked rhodium also has the disadvantage that the thermolabile rhodium catalyst (cf. U.S. Pat. No. 4,400,547) partially decomposes as a consequence of the heating during distillative work-up of the hydroformylation product, giving metallic rhodium, which deposits on the walls of the reactor and in the lines. The precipitated rhodium metal cannot be recycled into the hydroformylation reaction since it cannot be converted into the catalytically active rhodium compound under the hyroformylation conditions. The losses of rhodium resulting from this chemical behavior of naked rhodium catalysts have hitherto prevented relatively large-scale industrial application of this process.

DE-A 33 38 340 and U.S. Pat. No. 4,400,547 describe processes for hydroformylation by means of naked rhodium catalysts in which, in order to prevent deposition of rhodium, a phosphine or phosphite is added to the hydroformylation reaction product, protecting the rhodium catalyst by forming phosphine and/or phosphite complexes before thermal decomposition during distillative work-up of the hydroformylation products. When the distillation is complete, the rhodium-containing distillation residue is treated with an oxidant, which releases the rhodium in the catalytically active form from the phosphine or phosphite complexes in question and oxidizes the phosphine and phosphite ligands to the corresponding phosphine oxides and phosphates, which do not form rhodium complexes under hydroformylation conditions. The oxidized distillation residue is then re-employed as the hydroformylation catalyst. The oxidized phosphorus compounds formed on oxidation generally do not interfere with the hydroformylation, but, as a consequence of the process, accumulate in this hydroformylation circuit, with the consequence that a part-stream of this catalyst solution must be constantly removed from the hydroformylation circuit and replaced by fresh catalyst solution. The catalyst solution removed must be subjected to a special procedure for recovery of the rhodium present therein.

WO 82/03856 relates to a process for the thermal stabilization of unmodified, i.e. naked, rhodium catalysts in which the hydroformylation reaction product is treated with an oxygen-containing gas, causing a part amount of the aldehydes formed to be oxidized to the corresponding carboxylic acids, which form thermally stable rhodium carboxylates with the rhodium catalyst during distillative work-up which can be reused as hydroformylation catalysts. This process has the disadvantage of the reduction in yield as a consequence of the partial oxidation of the product aldehydes to carboxylic acids. In addition, it is restricted to hydroformylation reactions in which distillable products are formed; thus, for example, the rhodium catalysts in this process cannot be separated from the product of the hydroformylation of polyisobutene.

In order to prevent losses of rhodium, U.S. Pat. No. 3,984,478 has developed a hydroformylation process in which the hydroformylation is carried out in the presence of a sulfonated or unsulfonated phthalocyanine. Since some of the rhodium phthalocyanine complexes formed in this process have low solubility or are only soluble in water, but not in the organic hydroformylation medium, the hydroformylation is carried out either in the presence of the solid rhodium phthalocyanines or in a two-phase system with water. However, the coordinative bonding of the rhodium to the phthalocyanine in these complexes is very strong, which means that the rhodium remains bonded to the phthalocyanine even under the hydroformylation conditions. As a consequence, the hydroformylation takes place only at the hydroformylation medium/solid phthalocyanine interface or at the interface with the aqueous rhodium phthalocyanine complex solution; the reaction rate and thus also the space-time yield of the hydroformylation reaction are thus so low that this process cannot be operated economically.

It is an object of the present invention to provide a process for the preparation of aldehydes from long-chain and/or branched olefins with the aid of naked rhodium catalysts by means of which the problems of deposition of metallic rhodium during distillative work-up of the hydroformylation product and the removal of the rhodium catalyst from undistillable product aldehydes can be solved satisfactorily. To this end, the aim was to find a hydroformylation process in which complex ligands bind coordinatively to the rhodium catalyst in a reversible manner depending on the pressure of the carbon monoxide/hydrogen gas mixture, so that the catalyst is extractable during extractive work-up. After recycling into the hydroformylation reaction, the complexes formed in this way should decomplex reversibly under the reaction pressure used in the presence of the carbon monoxide/hydrogen gas mixture, and the liberated rhodium compound should re-adopt the catalytic properties of naked rhodium.

We have found that this object is achieved by a process for the preparation of aldehydes by hydroformylation of olefins having more than 7 carbon atoms, comprising hydroformylation by means of a rhodium catalyst dissolved homogeneously in the reaction medium, removal of the rhodium catalyst from the hydroformylation reaction product, and recycling of the rhodium separated off from the hydroformylation product into the hydroformylation step, wherein the rhodium catalyst is extracted from the hydroformylation product into the aqueous phase by means of an aqueous solution of a nitrogen-containing complexing agent from the group comprising of substituted or unsubstituted, sulfonated or sulfonated substituent-carrying pyridines, quinotines, 2,2'-bipyridines, 1,10-phenanthrolines, 2,2'-biquinolines, 2,2',6',2''-terpyridines and porphines, and/or from the group comprising of carboxylated pyridines, carboxylated quinolines, substituted or unsubstituted, carboxylated or carboxylated substituent-carrying 2,2'-bipyridines, 1,10-phenanthrolines, 2,2'-biquinolines, 2,2',6',2''-terpyridines and porphines, and the aqueous, rhodium-containing extract is recycled into the hydroformylation step.

According to the invention, the rhodium-containing hydroformylation products obtained on hydroformylation by means of naked rhodium are treated with water-soluble, nitrogen-containing, preferably multidentate complexing agents which form complexes with the rhodium catalyst which are hydrophilic and, as a consequence of their good water solubility, can be extracted from the organic hydroformylation medium with water. After removal of the rhodium catalyst present in the hydroformylation product by extraction in the form of a water-soluble complex with the complexing agent employed according to the invention, the hydroformylation product can be worked up in a conventional manner, for example by isolating the hydroformylation product from the organic extract by distillation or by removing the relatively volatile organic constituents of the hydroformylation product from the less-volatile or even undistillable hydroformylation product by distillation. The aqueous extract of the hydroformylation product, which contains the rhodium catalyst now complexed by the nitrogen-containing complexing agent, is fed as such into the hydroformylation reactor. Under the carbon monoxide/hydrogen pressure prevailing therein, the rhodium is dissolved out of its water-soluble complex with the nitrogen-containing complexing agent employed according to the invention by the carbon monoxide, with re-formation of the lipophilic, water-insoluble naked rhodium catalyst, which then migrates out of the aqueous phase into the organic phase of the hydroformylation medium, where it again catalyses the hydroformylation of the olefins employed with the reactivity and selectivity characteristic of naked rhodium.

The complexing agents which form water-soluble complexes with the rhodium catalyst dissolved in the hydroformylation reaction product are preferably sulfonated, nitrogen-containing complexing agents, such as sulfonated pyridines or sulfonated quinolines and/or water-soluble carboxylated pyridines or quinolines. Preference is given to multidentate, in particular bidentate, tridentate or tetradentate, sulfonated, nitrogen-containing complexing agents, particularly preferably 2,2'-bipyridine sulfonates, 2,2'-biquinoline sulfonates, 1,10-phenanthroline sulfonates, 2,2',6',2''-terpyridine sulfonates or porphine sulfonates. Particular preference is likewise given in the process according to the invention to the use of multidentate, in particular bidentate, tridentate or tetradentate, carboxylated, nitrogen-containing complexing agents, in particular 2,2'-bipyridine carboxylates, 1,10-phenanthroline carboxylates, 2,2'-biquinoline carboxylates, 2,2',6',2''-terpyridine carboxylates and porphine carboxylates.

In the presence of these complexing agents, coordinative bonds to the rhodium central atom of the rhodium catalyst form, presumably via the free electron pair of the nitrogen atoms; presumably some of the carbon monoxide bonded to the central rhodium atom of the rhodium catalyst is reversibly displaced by these ligands under the conditions of the complexing. The presence of sulfonate or carboxylate groups in the nitrogen-containing complexing agents used according to the invention is critical for the feasibility of the process according to the invention. Complexing agents may contain one or more carboxylate and/or sulfonate groups per molecule, where the number of carboxylate and/or sulfonate groups in the molecule is of course also dependent on the size of the complexing agent molecule and on its reactivity with sulfonating reagents. For example, monosulfonated pyridines and 2,2'-bipyridines are generally used as complexing agents, whereas, by contrast, the sulfonated porphines may contain, for example, four sulfonate groups in the molecule. Since carboxylate-carrying, nitrogen-containing complexing agents can advantageously be prepared by oxidizing the corresponding alkyl-, preferably methyl-substituted complexing agents, which are readily available by conventional chemical processes, the carboxylated complexing agents may carry from 1 to 6, preferably from 1 to 4, particularly preferably from 1 to 3, carboxyl groups, depending on the size of the molecule. The number of carboxyl and/or sulfonyl groups in the complexing agent molecule affects the solubility of these complexing agents in water. It is of course also possible for nitrogen-containing complexing agents containing both carboxyl groups and sulfonyl groups as substituents, or mixtures of sulfonated and carboxyl-containing complexing agents to be used in the process according to the invention. The sulfonate and carboxylate groups are preferably in salt form in the complexing agents used according to the invention, in particular in the form of water-soluble salts, particularly preferably in the form of their onium, alkali metal and/or alkaline earth metal salts. The type of onium salt used is generally not crucial. Thus, for example, ammonium, phosphonium or arsonium salts of the carboxylic or sulfonic acids in question can be employed. In order to avoid misunderstandings, it is expressly pointed out at this point that the nitrogen-containing complexing agent sulfonates or carboxylates which can be used according to the invention carry the sulfonate or carboxylate groups as substituents and are not bonded to any sulfonate or carboxylate anions, for example in the form of a salt.

Said complexing agents may additionally be substituted by substituents which are inert under the reaction conditions, such as halogen atoms, in particular fluorine, chlorine or bromine atoms, alkyl groups, in particular $C_1$- to $C_4$-alkyl groups, aryl groups, in particular $C_6$- to $C_{10}$-aryl groups, $C_7$- to $C_{12}$-aralkyl groups, the nitro group, the hydroxyl group, the cyano group, alkoxy groups, in particular $C_1$- to $C_4$-alkoxy groups, and $C_1$- to $C_{10}$-alkylsulfonate groups.

Substitution by alkyl, aryl or aralkyl groups may be advantageous, in particular, if the nitrogen-containing complexing agent is inert and can only be sulfonated under drastic conditions. Since carbocyclic aryl and aralkyl groups are frequently easier to sulfonate than electron-deficient, nitrogen-containing heterocycles, such as pyridine or bipyridine, the sulfonation in the case of this type of substitution of the heterocycle or in the case of fusing of aromatic, non-heterocyclic ring systems to the nitrogen-containing heterocycle, can be carried out under significantly milder conditions without these nitrogen-containing complexing agents substituted in this way having their property as complexing agent for the process according to the invention impaired by such a substitution. A similar situation also applies to the case of alkyl substitution of the nitrogen-containing complexing agent, since the aliphatic side chains can generally readily, for example by means of sulfuryl chloride, be converted into the corresponding sulfochlorides, basic hydrolysis of which gives the corresponding sulfonates.

The sulfonated, nitrogen-containing complexing agents can be produced from the corresponding unsulfonated parent compounds by sulfonation processes which are conventional per se, such as reaction with concentrated sulfuric acid or oleum, in the presence or absence of catalysts, such as mercury sulfate, or by reacting these compounds with halosulfonic acids, preferably chlorosulfonic acid, and subsequently hydrolysing the sulfonyl halides formed to give the sulfonic acid salts. Alkane sulfonate-substituted complexing agents, such as pyridine 4-ethane sulfonate, can be obtained, for example, by sulfochlorination of the corresponding parent compounds, 4-ethylpyridine in this case, by means of sulfuryl chloride, and subsequent alkaline hydrolysis of the sulfochloride formed. These and other methods which can be used for the preparation of the sulfonated complexing agents are described in C. Ferri, Reaktionen der organischen Synthese, pp. 165–172 and pp. 484–485, Thieme, Stuttgart, 1978. For example, 2,2'-bipyridine-5-sulfonic acid can be obtained by sulfonating 2,2'-bipyridine by the method of Herrmann et al., Chem. Ber. 123 (1990) 1953. 1,10-Phenanthroline can be sulfonated in an analogous manner. Further sulfo-substituted bipyridines can be prepared by the method of Campa et al., An. Quim., Ser. C 84 (1988) 128. The terpyridines, which can be prepared, for example, by the methods indicated by Kröhnke in Synthesis 1 (1976), can likewise be converted into the corresponding sulfonates by the methods indicated by Ferri.

On sulfonation of the nitrogen-containing complexing agents by the methods indicated above, isomer mixtures of the sulfonated complexing agents are generally formed, carrying the sulfonate groups in the various possible positions of the nitrogen-containing complexing agent ring system and/or on the substituents bonded to the complexing agent ring system, in particular on the aromatic substituents, such as the phenyl or naphthyl substituents. In addition, in particularly in relatively complex complexing agent ring systems and in complexing agents substituted by aromatic substituents, multiple sulfonation of these complexing agents frequently occurs. The complexing agent sulfonate mixtures, comprising isomeric, monosulfonated complexing agents and polysulfonated complexing agents, obtained in this way by various sulfonation methods can of course be resolved into the individual sulfonated components by the methods of the prior art, such as crystallization or ion exchange chromatography, and the resultant individual components can be employed as complexing agents in the process according to the invention, but since the site of sulfonation and the degree of sulfonation of the sulfonated complexing agents are generally not crucial to the result of the process according to the invention and in general the only important factor for the success of the process according to the invention is that the nitrogen-containing complexing agents are sulfonated, the complexing agent sulfonate mixtures obtained by the various sulfonation methods, advantageously after conversion into their water-soluble salts, are preferably used in the process according to the invention, which makes separation into the individual sulfonated components of the complexing agent sulfonating mixture superfluous. For this reason, this application generally does not refer to the individual sulfonates of the various complexing agents, but instead denotes the complexing agents in question in groups, for example as quinoline sulfonates, 2,2'-biquinoline sulfonates, 1,10-phenanthroline sulfonates, terpyridine sulfonates, etc. Only in exceptional cases, if a certain sulfonation method for sulfonation of specific complexing agents gives the sulfonated complexing agent in question virtually exclusively under the reaction conditions usually used, are the individual sulfonated complexing agents mentioned by name in this application.

In order to illustrate the wide range of complexing agents which can be used according to the invention, a number of nitrogen-containing complexing agents which, after sulfonation, corresponding to the abovementioned methods, and conversion into their salts, can be employed in the process according to the invention are mentioned below by way of example: pyridine, picolines, other alkylpyridines, quinoline, 5,6-benzoquinoline, 2,2'-bipyridine, 2,2'-biquinoline of the formula I

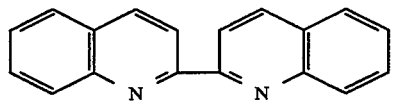

5,6,5',6'-dibenzo-2,2'-biquinoline of the formula II

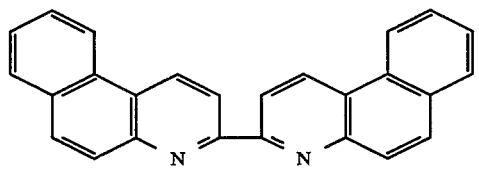

1,10-phenanthroline, 2,9-dimethylphenanthroline, 4,7-diphenyl-1,10-phenanthroline (bathophenanthroline) of the formula III

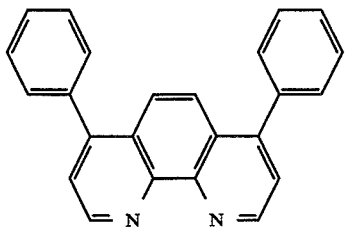

2,9-dimethyl-4,7-diphenyl-1,10-phenanthroline (bathocuproin) of the formula IV

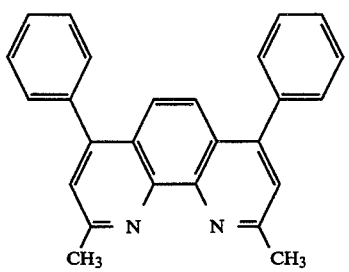

4,5-diazafluorene of the formula V

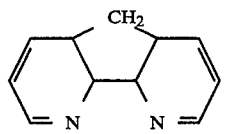

dipyrido[3,2-a: 2',3'-c]phenazine of the formula VI

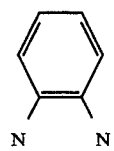

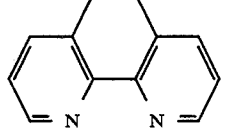

(compounds V and VI are obtainable by the method of Aust. J. Chem. 23 (1970) 1023), 2,2',6',2''-terpyridine of the formula VII

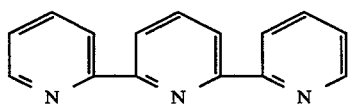

4''-phenyl-2,2',6',2''-terpyridine of the formula VIII

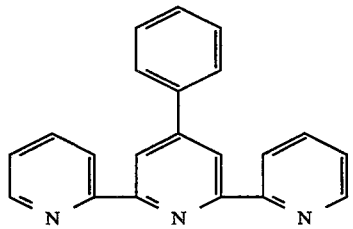

4-methyl(4'-phenyl) (4''-methyl)-2,2',6',2''-terpyridine of the formula IX

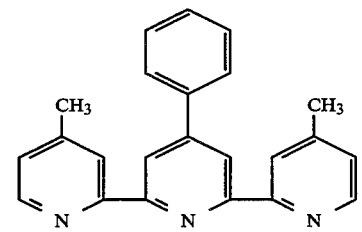

and porphines.

Sulfonated, nitrogen-containing complexing agents which are particularly suitable for the process according to the invention are those whose properties as complexing agents can be attributed to the 2,2'-bipyridine, 1,10-phenanthroline or 2,2',6',2''-terpyridine ring system they contain, as is the case, for example, in the abovementioned compounds of the formulae I to IX.

The carboxyl-carrying complexing agents can be prepared from the mono- to hexa-, preferably mono- to tetra-, particularly preferably mono- to tri-methyl-substituted compounds I to IX by oxidation of the methyl groups, for example by means of potassium permanganate. The methyl-substituted or benzo-fused compounds I to IX can be obtained, for example, by the processes described by Kröhnke et al., Synthesis 1 (1976), Sasse et al., J. Chem. Soc. (1956) 616, Sasse et al., J. Heterocycl. Chem. 8 (1971) 483, Bos et al., Synth. Commun. 9 (1979) 497, and Elliot et al., J. Am. Chem. Soc. 104 (1982) 7519. The oxidation of the methyl groups to carboxyl groups can be carried out, for example, using potassium permanganate by the methods which can generally be used, as described by Anderson et al. (J. Chem. Soc. Dalton Trans. (1985) 2247) or Hanabusa et al. (Makromol. Chem. 190 (1989) 1). Preferred carboxyl-carrying, nitrogen-containing complexing agents are 2,2'-bipyridine-4,4'-dicarboxylic acid and 2,2'-bipyridine-5,5'-dicarboxylic acid, and salts thereof.

In the process according to the invention, the hydroformylation product from the hydroformylation using naked rhodium, which, in addition to the product aldehyde, also contains, inter alia, unreacted olefins and products from hydrogenation of the product aldehyde, for example the corresponding alcohols, if used a solvent, such as aromatic or aliphatic hydrocarbons, or relatively high-molecular-weight condensation products of the aldehydes formed during the hydroformylation, and the rhodium catalyst homogeneously dissolved in the hydroformylation product, is treated with the aqueous solution of the complexing agent employed in each case, an aqueous/organic two-phase system forming, and the rhodium dissolved in the organic phase is extracted into the aqueous phase, after complexing, from the complexing agent employed. The addition of a phase-transfer catalyst is not necessary, but is possible.

The hydroformylation can be carried out in the presence or absence of organic solvents. Particularly advantageous is the use of organic solvents, in particular in the case of hydroformylation of long-chain or polymeric olefins. The solvents which can be used are the solvents usually employed in hydroformylation processes, for example high-boiling aromatic and aliphatic hydrocarbons, or high-boiling aldehyde condensation products, formed during the hyroformylation as a by-product as a consequence of condensation of the product aldehydes.

The hydroformylation product is expediently decompressed to atmospheric pressure before its extraction, although it is possible to carry out the extraction under superatmospheric pressure or reduced pressure. The extraction is generally carried out at from 20° to 150° C., preferably at from 50° to 120° C.

In order to achieve a high degree of extraction of the rhodium from the organic phase of the hydroformylation product, a rhodium/complexing agent molar ratio of at least ½, but preferably from 1/10 to 1/200, is selected.

The extraction of the rhodium from the organic phase can be carried out either in air or under a protective-gas atmosphere. The use of a protective-gas atmosphere, for example a nitrogen or argon atmosphere, is particularly advantageous if oxidation-sensitive hydroformylation products are formed. Highly efficient extraction requires thorough mixing of the organic and aqueous phases, as can be achieved by means of conventional extraction apparatuses, such as mixer-settler apparatuses, bubble columns and countercurrent extraction apparatuses. The transfer of the rhodium into the aqueous phase can, if desired, be monitored photometrically from its red coloration.

The hydroformylation products freed from the rhodium catalyst can be worked up in a conventional manner. The aqueous, rhodium-containing extract is advantageously recycled into the hydroformylation step. Under the reaction conditions usually prevailing therein (a $CO/H_2$ molar ratio of from 1/5 to 5/1, preferably from ½ to 2/1, a total pressure of from 10 to 1000 bar, preferably from 90 to 350 bar, and a temperature of from 50° to 170° C. in particular from 80° to 140° C.), the rhodium coordinatively bonded to the complexing agent employed is dissolved out of the water-soluble complex by the carbon monoxide, and the naked, lipophilic rhodium catalyst is re-formed and extracted into the organic phase of the hydroformylation medium, while the hydrophilic complexing agent, which is now rhodium-free, remains in the aqueous phase. Efficient utilization of this effect requires thorough mixing of the organic phase of the hydroformylation medium with the aqueous solution of the rhodium/complexing agent complex, which is why the hydroformylation can advantageously be carried out, for example, in stirred autoclaves or in tubular reactors provided with flow modifiers, such as baffles.

The ratio between the volume of the hydroformylation medium and the volume of the aqueous rhodium complex solution is in principle unimportant, but for purely economic reasons it is desired to keep the proportion of the aqueous phase as low as possible compared with the total volume of the aqueous and organic phases in the hydroformylation reactor. In general, an organic phase/aqueous phase ratio by volume of from 95/5 to 30/70, in particular from 90/10 to 50/50, is used in the hydroformylation.

When the hydroformylation is complete and the carbon monoxide partial pressure has been reduced to from 0 to 5 bar, preferably to from 0 to 2 bar, particularly preferably to 0 bar, the rhodium present in the hydroformylation product is re-extracted into the aqueous phase from the complexing agent, and the rhodium cycle can start afresh. The process according to the invention can thus be carried out either batchwise or continuously.

The process according to the invention is particularly suitable for the hydroformylation of olefins having more than 7 carbon atoms, in particular for the hydroformylation of $C_7$- to $C_{20}$-olefins, which may be straight-chain or branched and may contain $\alpha$-olefinic and/or internal double bonds, for example 1-octene, 1-dodecene or trimeric or tetrameric propylene. The aldehydes formed from these olefins are precursors in the preparation of plasticizer alcohols, which can be prepared therefrom in a conventional manner by hydrogenation. The process according to the invention is also particularly suitable for the hydroformylation of polymeric olefins, such as low-molecular-weight polyisobutene. The product of the hydroformylation of polyisobutene is converted by reductive amination, as described in EP-A 244 616, into polyisobutenamine, which is used as a fuel additive. The olefins employed for the hydroformylation can be prepared, for example, by acid-catalyzed elimination of water from the corresponding fatty alcohols or by a wide range of other industrial processes, as described, for example, in Weissermel and Arpe, Industrielle Organische Chemie, 2nd Edn., pp. 72–77 and pp. 80–85, Verlag Chemie, Weinheim, 1978, and low-molecular-weight polyisobutene can be produced by the process of EP-A 145 235.

EXAMPLES

Example 1

1-Dodecene was converted into the corresponding tridecanals in the presence of naked rhodium, with a rhodium content of the hydroformylation medium of 100 ppm, using synthesis gas ($CO/H_2$ molar ratio 1/1) at 100° C. and 100 bar. The naked rhodium catalyst had been produced from dicarbonylrhodium acetylacetonate in the hydroformylation medium under the hydroformylation conditions. 50 g of the hydroformylation product, whose rhodium content had dropped to 87 ppm as a consequence of the increase in weight caused by the reaction, were added at atmospheric pressure to a solution of 0.11 g of sodium 2,2'-bipyridine-5-sulfonate in 50 g of water, and the mixture was stirred at room temperature for half an hour. After this time, the organic phase contained 70 ppm of rhodium, and the aqueous phase contained 20 ppm. The two-phase mixture was heated to 100° C. with stirring and stirred at this temperature for a further hour. After this procedure, the organic phase contained less than 5 ppm of rhodium, and the rhodium content of the aqueous phase had risen to 85 ppm, corresponding to a degree of extraction of greater than 95%.

Example 2

49.8 g of an aqueous rhodium-containing extract solution obtained as in the process of Example 1 were reacted with the same volume of trimeric propylene at 100° C. and with synthesis gas ($CO/H_2$ molar ratio 1/1) at 150 bar for 3 hours. The olefin was then converted into the corresponding aldehydes in a conversion of 95% and a selectivity of 98%. The two-phase reaction product contained 9.8 mg of rhodium in the organic phase and 1.3 mg of rhodium in the aqueous phase. The two phases were mixed vigorously for 1 hour at 85° C. and at atmospheric pressure. The organic phase then contained 1.8 mg of rhodium, and the rhodium content of the aqueous phase was 9.0 mg.

The aqueous phase was recycled into the hydroformylation reactor, where it was mixed with the same volume of trimeric propylene, and the olefin was hydroformylated as described above. When the hydroformylation was complete, the trimeric propylene was converted into the corresponding aldehydes in a conversion of 94% and a selectivity of 98%. The two-phase reaction product contained 7.5 mg of rhodium in the organic phase and 1.5 mg of rhodium in the aqueous phase. After the organic phase had been extracted as described above, the rhodium content in the aqueous phase was 7.7 mg and that in the organic phase was 0.6 mg. The aqueous rhodium solution was re-employed for the hydroformylation under the stated conditions, and the respective aldehydes were obtained in an olefin conversion of 94% and a selectivity of 98%. The organic phase of the hydroformylation product contained 5.2 mg of rhodium and the aqueous phase contained 0.53 mg of rhodium.

The losses of rhodium during this series experiment were due to sampling for analytical purposes.

Example 3

43.8 g of an aqueous rhodium solution prepared by the process of Example 1 were reacted with synthesis gas and 50 g of 1-octene in an autoclave at 100° C. and 150 bar for 3 hours. When the reaction was complete, the hydroformylation product contained 1.24 mg of rhodium and the aqueous phase contained 1.43 mg of rhodium. After the extraction as described in Example 2, the rhodium content of the organic phase had dropped to 0.25 mg and that of the aqueous phase had risen to 2.53 mg. The hydroformylation conversion was 99%, with an aldehyde selectivity of 95%. The aqueous phase was re-employed for the hydroformylation, with virtually the same result as mentioned above.

Example 4

41.1 g of an aqueous rhodium solution prepared by the process of Example 1 were added to 37.7 g of polyisobutene (mean molecular weight about 1000) and 40 g of toluene, and the mixture was reacted at 130° C. and 280 bar of $CO/H_2$ for three hours. After the rhodium extraction, the organic phase was separated off and analyzed.

Yield: 93% of hydroformylation product

Example 5

100 g of trimeric propylene were reacted for 5 hours in the presence of 100 ppm of naked rhodium prepared in the hydroformylation medium as described in Example 1, at 130° C. and a synthesis gas pressure 280 bar. 50 g of the hydroformylation product, containing 5 mg (0.049 mol of rhodium), were treated with a solution of 602.1 mg (0.49 mol) of tetrasodium mesotetra(4-sulfophenyl)porphine dodecahydrate (prepared as described in J. Org. Chem. 38 (1973) 2103) in 50 ml of water, and the mixture was stirred for 3 hours at 85° C. in air. The aqueous phase then contained 95 ppm of rhodium, and 3 ppm of rhodium remained in the organic phase, corresponding to a degree of extraction of 97%.

Example 6

50 g of a trimeric propylene hydroformylation product containing 70 ppm of naked rhodium was mixed vigorously at 85° C. with 50 g of an aqueous solution of 135 mg of sodium 1,10-phenanthrolinesulfonate.1.5 $H_2O$. After 2 hours, the aqueous phase contained 65 ppm of rhodium, corresponding to a degree of extraction of 93%.

Sodium 1,10-phenanthrolinesulfonate.1.5 $H_2O$ had been prepared from 1,10-phenanthroline analogously to the process for the sulfonation of 2,2'-bipyridine (cf. Chem. Ber. 123 (1990) 1953).

Another process for the sulfonation of 1,10-phenanthroline is given in Anal. Chem. 33 (1961) 867.

Example 7

1484 g of trimeric propylene and 36.1 mg of $Rh(CO)_2acac$ were introduced into an autoclave, 100 bar of $CO/H_2$ in a molar ratio of 1/1 were injected, the autoclave was decompressed and compressed again and heated to 130° C., and $CO/H_2$ was injected to a pressure of 280 bar. After three hours, the reaction mixture was cooled, decompressed and discharged. After filtration, the hydroformylation product contained 74 ppm of rhodium. 120 g of this product was mixed under argon with 319 mg of disodium 2,2'-bipyridine-4,4'-dicarboxylate hydrate (0.9 mmol) in 120 ml of water, and the mixture was heated to 85° C. while stirring vigorously. After 90 minutes, the aqueous phase contained 71 ppm of rhodium and the organic phase 7 ppm of rhodium, which corresponds to a degree of extraction of 92.92%. acac=acetylacetonate.

We claim:

1. A process for the preparation of aldehydes by hydroformylation of olefins having more than 7 carbon atoms, comprising hydroformylation in the presence of synthesis gas by means of a naked rhodium catalyst dissolved homogeneously in the reaction medium, removal of said naked rhodium catalyst from the hydroformylation reaction product, and recycling of said naked rhodium separated off from the hydroformylation product into the hydroformylation step, wherein said naked rhodium catalyst is extracted from the hydroformylation product into the aqueous phase by means of an aqueous solution of a nitrogen-containing complexing agent selected from the group consisting of substituted or unsubstituted, sulfonated or sulfonated substituent-carrying 2,2'-bipyridines, 1,10-phenanthrolines, 2,2'-biquinolines, 2,2',6',2''-terpyridines and porphines, or from the group consisting of substituted or unsubstituted, carboxylated or carboxylated substituent-carrying 2,2'-bipyridines, 1,10-phenanthrolines, 2,2'-biquinolines, 2,2',6',2''-terpyridines and porphines, or mixtures of said sulfonated or carboxyl-containing complexing agents, and the aqueous, rhodium-containing extract is recycled into the hydroformylation step.

2. A process as claimed in claim 1, wherein the complexing agent used is a 2,2'-bipyridine sulfonate, a 1,10-phenanthroline sulfonate, a 2,2'-biquinoline sulfonate or a 2,2',6',2''-terpyridine sulfonate.

3. A process as claimed in claim 1, wherein the complexing agent used is a water-soluble salt of 2,2'-bipyridine-5-sulfonic acid.

4. A process as claimed in claim 1, wherein the complexing agent used is a 2,2'-bipyridine dicarboxylate, a 1,10-phenanthroline dicarboxylate, a 2,2'-biquinoline dicarboxylate or a 2,2',6',2''-terpyridine dicarboxylate.

5. A process as claimed in claim 1, wherein the complexing agent used is a water-soluble salt of 2,2'-bipyridine-4,4'-dicarboxylic acid and/or of 2,2'-bipyridine-5,5'-dicarboxylic acid.

* * * * *